United States Patent [19]

Houghten et al.

[11] Patent Number: 5,294,605
[45] Date of Patent: Mar. 15, 1994

[54] AMPHIPHILIC PEPTIDE COMPOSITIONS AND ANALOGUES THEREOF

[75] Inventors: Richard A. Houghten, Solana Beach; Sylvie Blondelle, La Jolla, both of Calif.

[73] Assignee: The Scripps Research Institute, La Jolla, Calif.

[21] Appl. No.: 725,331

[22] Filed: Jul. 8, 1991

Related U.S. Application Data

[63] Continuation-in-part of Ser. No. 554,422, Jul. 19, 1990, abandoned.

[51] Int. Cl.$^5$ .................. A61K 37/02; C07K 7/08; C07K 7/10
[52] U.S. Cl. ........................... 514/13; 514/12; 530/324; 530/325; 530/326; 530/327
[58] Field of Search ............... 514/12, 13; 530/327, 530/326, 325, 324

[56] References Cited

U.S. PATENT DOCUMENTS 4,507,230 3/1985 Tam et al. ............... 530/337
4,810,777 3/1989 Zasloff .................... 514/12

FOREIGN PATENT DOCUMENTS 04371 5/1989 PCT Int'l Appl. .

OTHER PUBLICATIONS

Blondelle et al., *Biochemistry*, 31:12688–12694 (1992).

*Primary Examiner*—Lester L. Lee
*Attorney, Agent, or Firm*—Dressler, Goldsmith, Shore & Milnamow, Ltd.

[57] ABSTRACT

A process for inhibiting growth of a target cell comprising administering to a host or to a target cell or virus a biologically active peptide which includes one of the following basic structures; $R_1$-$R_1$-$R_2$-$R_1$-$R_1$-$R_2$-$R_2$-$R_1$-$R_1$-$R_2$-$R_2$-$R_1$-$R_2$-$R_2$; $R_2$-$R_1$-$R_1$-$R_2$-$R_2$-$R_1$-$R_2$-$R_2$-$R_1$-$R_1$-$R_2$-$R_2$-$R_1$-$R_1$; or $R_1$-$R_2$-$R_1$-$R_1$-$R_2$-$R_2$-$R_1$-$R_1$-$R_2$-$R_2$-$R_1$-$R_2$-$R_2$-$R_1$-$R_1$-$R_2$-$R_2$-$R_1$, wherein $R_1$ is a hydrophobic amino acid, and $R_2$ is a basic hydrophilic or neutral hydrophilic amino acid. A preferred peptide is of the structural formula:

(SEQ ID NO:3).

Substitution and deletion analogues of this peptide can be prepared that have increased biological activity. Such peptides can be employed as pharmaceuticals.

31 Claims, No Drawings

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may be acetylated at N-terminus.

( x ) PUBLICATION INFORMATION:
        ( A ) AUTHORS: Houghten, R.
                     Ostresh, J.
        ( B ) JOURNAL: Bio Chromatography
        ( D ) VOLUME: 2
        ( E ) ISSUE: 2
        ( F ) PAGES: 80-83
        ( G ) DATE: 1987

( x i ) SEQUENCE DESCRIPTION: SEQ ID NO:1:

```
Leu  Leu  Lys  Leu  Leu  Lys  Lys  Leu  Leu  Lys
1                   5                        10
Lys  Leu  Lys  Lys
```

( 2 ) INFORMATION FOR SEQ ID NO:2:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may be acetylated at N-terminus.

( x ) PUBLICATION INFORMATION:
        ( A ) AUTHORS: Houghten, R.
                     Ostresh, J.
        ( B ) JOURNAL: Bio Chromatography
        ( D ) VOLUME: 2
        ( E ) ISSUE: 2
        ( F ) PAGES: 80-83
        ( G ) DATE: 1987

( x i ) SEQUENCE DESCRIPTION: SEQ ID NO:2:

```
Lys  Leu  Leu  Lys  Leu  Lys  Lys  Leu  Leu
1                   5                        10
Lys  Lys  Leu  Leu
```

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus.

( x i ) SEQUENCE DESCRIPTION:SEQ ID NO:3:

```
Leu Lys Leu Leu Lys Lys Leu Leu Lys Lys
1               5                   10
Leu Lys Lys Leu Leu Lys Lys Leu
15
```

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus.

( x i ) SEQUENCE DESCRIPTION:SEQ ID NO:4:

```
Leu Leu Lys Lys Leu Lys Lys Leu Leu Lys
1               5                   10
Lys Leu Leu Lys Leu Leu
15
```

( 2 ) INFORMATION FOR SEQ ID NO:5:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus. Xaa is
            Met or methionine sulfoxide.

( x i ) SEQUENCE DESCRIPTION:SEQ ID NO:5:

```
Xaa Lys Leu Leu Lys Lys Leu Leu Lys Lys
1               5                   10
Leu Lys Lys Leu Leu Lys Lys Leu
15
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus. Xaa is
            Met or methionine sulfoxide.

( x i ) SEQUENCE DESCRIPTION:SEQ ID NO:6:

```
Leu Xaa Leu Leu Lys Lys Leu Leu Lys Lys
```

```
                    1                 5                          10
                 Leu Lys Lys Leu Leu Lys Lys Leu
                 15
```

(2) INFORMATION FOR SEQ ID NO:7:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: May be a C-terminal amide, and/or may
            be acetylated at N-terminus, Xaa is
            Met or methionine sulfoxide.

(xi) SEQUENCE DESCRIPTION:SEQ ID NO:7:

```
                 Leu Lys Xaa Leu Lys Lys Leu Leu Lys Lys
                 1               5                       10
                 Leu Lys Lys Leu Leu Lys Lys Leu
                 15
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: May be a C-terminal amide, and/or may
            be acetylated at N-terminus, Xaa is
            Met or methionine sulfoxide.

(xi) SEQUENCE DESCRIPTION:SEQ ID NO:8:

```
                 Leu Lys Leu Xaa Lys Lys Leu Leu Lys Lys
                 1               5                       10
                 Leu Lys Lys Leu Leu Lys Lys Leu
                 15
```

(2) INFORMATION FOR SEQ ID NO:9:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: May be a C-terminal amide, and/or may
            be acetylated at N-terminus, Xaa is
            Met or methionine sulfoxide.

(xi) SEQUENCE DESCRIPTION:SEQ ID NO:9:

```
                 Leu Lys Leu Leu Xaa Lys Leu Leu Lys Lys
                 1               5                       10
                 Leu Lys Lys Leu Leu Lys Lys Leu
                 15
```

(2) INFORMATION FOR SEQ ID NO:10:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (ix) FEATURE:

(D) OTHER INFORMATION: May be a C-terminal amide, and/or may be acetylated at N-terminus, Xaa is Met or methionine sulfoxide.

(xi) SEQUENCE DESCRIPTION:SEQ ID NO:10:
```
Leu Lys Leu Leu Lys Xaa Leu Leu Lys Lys
1               5                   10
Leu Lys Lys Leu Leu Lys Lys Leu
15
```

(2) INFORMATION FOR SEQ ID NO:11:

(i) SEQUENCE CHARACTERISTICS:
    (A) LENGTH: 18 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: May be a C-terminal amide, and/or may be acetylated at N-terminus, Xaa is Met or methionine sulfoxide.

(xi) SEQUENCE DESCRIPTION:SEQ ID NO:11:
```
Leu Lys Leu Leu Lys Lys Xaa Leu Lys Lys
1               5                   10
Leu Lys Lys Leu Leu Lys Lys Leu
15
```

(2) INFORMATION FOR SEQ ID NO:12:

(i) SEQUENCE CHARACTERISTICS:
    (A) LENGTH: 18 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: May be a C-terminal amide, and/or may be acetylated at N-terminus, Xaa is Met or methionine sulfoxide.

(xi) SEQUENCE DESCRIPTION:SEQ ID NO:12:
```
Leu Lys Leu Leu Lys Lys Leu Xaa Lys Lys
1               5                   10
Leu Lys Lys Leu Leu Lys Lys Leu
15
```

(2) INFORMATION FOR SEQ ID NO:13:

(i) SEQUENCE CHARACTERISTICS:
    (A) LENGTH: 18 amino acids
    (B) TYPE: amino acid
    (C) STRANDEDNESS:
    (D) TOPOLOGY: linear (ii) MOLECULE TYPE: peptide (ix) FEATURE:
    (D) OTHER INFORMATION: May be a C-terminal amide, and/or may be acetylated at N-terminus, Xaa is Met or methionine sulfoxide.

(xi) SEQUENCE DESCRIPTION:SEQ ID NO:13:
```
Leu Lys Leu Leu Lys Lys Leu Leu Xaa Lys
1               5                   10
Leu Lys Lys Leu Leu Lys Lys Leu
15
```

(2) INFORMATION FOR SEQ ID NO:14:

(i) SEQUENCE CHARACTERISTICS:
    (A) LENGTH: 18 amino acids
    (B) TYPE: amino acid (C) STRANDEDNESS:
(D) TOPOLOGY: linear (ii) MOLECULE TYPE: peptide (ix) FEATURE:
(D) OTHER INFORMATION: May be a C- terminal amide, and/or may
be acetylated at N-terminus, Xaa is
Met or methionine sulfoxide.

(xi) SEQUENCE DESCRIPTION:SEQ ID NO:14:

```
Leu Lys Leu Leu Lys Lys Leu Leu Lys Xaa
1               5                    10
Leu Lys Lys Leu Leu Lys Lys Leu
15
```

(2) INFORMATION FOR SEQ ID NO:15:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C- terminal amide, and/or may
be acetylated at N-terminus, Xaa is
Met or methionine sulfoxide.

(xi) SEQUENCE DESCRIPTION:SEQ ID NO:15:

```
Leu Lys Leu Leu Lys Lys Leu Leu Lys Lys
1               5                    10
Xaa Lys Lys Leu Leu Lys Lys Leu
15
```

(2) INFORMATION FOR SEQ ID NO:16:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C- terminal amide, and/or may
be acetylated at N-terminus, Xaa is
Met or methionine sulfoxide.

(xi) SEQUENCE DESCRIPTION:SEQ ID NO:16:

```
Leu Lys Leu Leu Lys Lys Leu Leu Lys Lys
1               5                    10
Leu Xaa Lys Leu Leu Lys Lys Leu
15
```

(2) INFORMATION FOR SEQ ID NO:17:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C- terminal amide, and/or may
be acetylated at N-terminus, Xaa is
Met or methionine sulfoxide.

(xi) SEQUENCE DESCRIPTION:SEQ ID NO:17:

```
Leu Lys Leu Leu Lys Lys Leu Leu Lys Lys
1               5                    10
Leu Lys Xaa Leu Leu Lys Lys Leu
15
```

( 2 ) INFORMATION FOR SEQ ID NO:18:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C-terminal amide, and/or may
        be acetylated at N-terminus, Xaa is
        Met or methionine sulfoxide.

( x i ) SEQUENCE DESCRIPTION:SEQ ID NO:18:

```
Leu Lys Leu Leu Lys Lys Leu Leu Lys Lys
1               5                   10
Leu Lys Lys Xaa Leu Lys Lys Leu
            15
```

( 2 ) INFORMATION FOR SEQ ID NO:19:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C-terminal amide, and/or may
        be acetylated at N-terminus, Xaa is
        Met or methionine sulfoxide.

( x i ) SEQUENCE DESCRIPTION:SEQ ID NO:19:

```
Leu Lys Leu Leu Lys Lys Leu Leu Lys Lys
1               5                   10
Leu Lys Lys Leu Xaa Lys Lys Leu
            15
```

( 2 ) INFORMATION FOR SEQ ID NO:20:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C-terminal amide, and/or may
        be acetylated at N-terminus, Xaa is
        Met or methionine sulfoxide.

( x i ) SEQUENCE DESCRIPTION:SEQ ID NO:20:

```
Leu Lys Leu Leu Lys Lys Leu Leu Lys Lys
1               5                   10
Leu Lys Lys Leu Leu Xaa Lys Leu
            15
```

( 2 ) INFORMATION FOR SEQ ID NO:21:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C-terminal amide, and/or may
        be acetylated at N-terminus, Xaa is
        Met or methionine sulfoxide.

( x i ) SEQUENCE DESCRIPTION:SEQ ID NO:21:

```
Leu  Lys  Leu  Leu  Lys  Lys  Leu  Leu  Lys  Lys
1                  5                        10
Leu  Lys  Lys  Leu  Leu  Lys  Xaa  Leu
15
```

( 2 ) INFORMATION FOR SEQ ID NO:22:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
        be acetylated at N-terminus, Xaa is
        Met or methionine sulfoxide.

( x i ) SEQUENCE DESCRIPTION:SEQ ID NO:22:

```
Leu  Lys  Leu  Leu  Lys  Lys  Leu  Leu  Lys  Lys
1                  5                        10
Leu  Lys  Lys  Leu  Leu  Lys  Lys  Xaa
15
```

( 2 ) INFORMATION FOR SEQ ID NO:23:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
        be acetylated at N-terminus.

( x i ) SEQUENCE DESCRIPTION:SEQ ID NO:23:

```
Lys  Lys  Leu  Leu  Lys  Lys  Leu  Leu  Lys  Lys
1                  5                        10
Leu  Lys  Lys  Leu  Leu  Lys  Lys  Leu
15
```

( 2 ) INFORMATION FOR SEQ ID NO:24:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
        be acetylated at N-terminus.

( x i ) SEQUENCE DESCRIPTION:SEQ ID NO:24:

```
Leu  Lys  Lys  Leu  Lys  Lys  Leu  Leu  Lys  Lys
1                  5                        10
Leu  Lys  Lys  Leu  Leu  Lys  Lys  Leu
15
```

( 2 ) INFORMATION FOR SEQ ID NO:25:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:

(D) OTHER INFORMATION: May be a C-terminal amide, and/or may be acetylated at N-terminus.

(x i) SEQUENCE DESCRIPTION:SEQ ID NO:25:

```
Leu  Lys  Leu  Lys  Lys  Lys  Leu  Leu  Lys  Lys
1                    5                        10
Leu  Lys  Lys  Leu  Leu  Lys  Lys  Leu
         15
```

(2) INFORMATION FOR SEQ ID NO:26:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C-terminal amide, and/or may be acetylated at N-terminus.

(x i) SEQUENCE DESCRIPTION:SEQ ID NO:26:

```
Leu  Lys  Leu  Leu  Lys  Lys  Lys  Leu  Lys  Lys
1                    5                        10
Leu  Lys  Lys  Leu  Leu  Lys  Lys  Leu
         15
```

(2) INFORMATION FOR SEQ ID NO:27:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C-terminal amide, and/or may be acetylated at N-terminus.

(x i) SEQUENCE DESCRIPTION:SEQ ID NO:27:

```
Leu  Lys  Leu  Leu  Lys  Lys  Leu  Lys  Lys  Lys
1                    5                        10
Leu  Lys  Lys  Leu  Leu  Lys  Lys  Leu
         15
```

(2) INFORMATION FOR SEQ ID NO:28:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: May be a C-terminal amide, and/or may be acetylated at N-terminus.

(x i) SEQUENCE DESCRIPTION:SEQ ID NO:28:

```
Leu  Lys  Leu  Leu  Lys  Lys  Leu  Leu  Lys  Lys
1                    5                        10
Lys  Lys  Lys  Leu  Leu  Lys  Lys  Leu
         15
```

(2) INFORMATION FOR SEQ ID NO:29:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide ( i x ) FEATURE:
    ( D ) OTHER INFORMATION: May be a C- terminal amide, and/or may
        be acetylated at N-terminus.

( x i ) SEQUENCE DESCRIPTION:SEQ ID NO:29:
    Leu Lys Leu Leu Lys Lys Leu Leu Lys Lys
    1               5                   10
    Leu Lys Lys Lys Leu Lys Lys Leu
    15

( 2 ) INFORMATION FOR SEQ ID NO:30:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus.

( x i ) SEQUENCE DESCRIPTION:SEQ ID NO:30:
        Leu Lys Leu Leu Lys Lys Leu Leu Lys Lys
        1               5                   10
        Leu Lys Lys Leu Lys Lys Lys Leu
        15

( 2 ) INFORMATION FOR SEQ ID NO:31:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, and/or may
            be acetylated at N-terminus.

( x i ) SEQUENCE DESCRIPTION:SEQ ID NO:31:
        Leu Lys Leu Leu Lys Lys Leu Leu Lys Lys
        1               5                   10
        Leu Lys Lys Leu Leu Lys Lys Lys
        15

( 2 ) INFORMATION FOR SEQ ID NO:32:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated at
            N- terminus.

( x i ) SEQUENCE DESCRIPTION:SEQ ID NO:32:
        Leu Lys Leu Lys Lys Lys Leu Leu Lys Lys
        1               5                   10
        Lys Lys Lys Leu Leu Lys Lys Leu
        15

( 2 ) INFORMATION FOR SEQ ID NO:33:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
  ( D ) OTHER INFORMATION: C-terminal amide, acetylated at
    N-terminus.

( x i ) SEQUENCE DESCRIPTION:SEQ ID NO:33:
```
Leu Lys Leu Arg Lys Lys Leu Leu Lys Lys
1               5                   10
Arg Lys Lys Leu Leu Lys Lys Leu
15
```

( 2 ) INFORMATION FOR SEQ ID NO:34:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: C-terminal amide, acetylated at
      N-terminus.

( x i ) SEQUENCE DESCRIPTION:SEQ ID NO:34:
```
Leu Lys Leu His Lys Lys Leu Leu Lys Lys
1               5                   10
His Lys Lys Leu Leu Lys Lys Leu
15
```

( 2 ) INFORMATION FOR SEQ ID NO:35:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: C-terminal amide, acetylated
      at N-terminus.

( x i ) SEQUENCE DESCRIPTION:SEQ ID NO:35:
```
Leu Lys Leu Ser Lys Lys Leu Leu Lys Lys
1               5                   10
Ser Lys Lys Leu Leu Lys Lys Leu
15
```

( 2 ) INFORMATION FOR SEQ ID NO:36:

( i ) SEQUENCE CHARACTERISTICS:
    ( A ) LENGTH: 18 amino acids
    ( B ) TYPE: amino acid
    ( C ) STRANDEDNESS:
    ( D ) TOPOLOGY: linear ( i i ) MOLECULE TYPE: peptide ( i x ) FEATURE:
    ( D ) OTHER INFORMATION: C-terminal amide, acetylated at
      N-terminus.

( x i ) SEQUENCE DESCRIPTION:SEQ ID NO:36:
```
Leu Lys Leu Met Lys Lys Leu Leu Lys Lys
1               5                   10
Met Lys Lys Leu Leu Lys Lys Leu
15
```

( 2 ) INFORMATION FOR SEQ ID NO:37:

( i ) SEQUENCE CHARACTERISTICS:
    ( A ) LENGTH: 18 amino acids
    ( B ) TYPE: amino acid (C) STRANDEDNESS:
(D) TOPOLOGY: linear (ii) MOLECULE TYPE: peptide (ix) FEATURE:
(D) OTHER INFORMATION: C-terminal amide, acetylated
at N-terminus, Xaa is methionine
sulfoxide.

(xi) SEQUENCE DESCRIPTION:SEQ ID NO:37:

```
Leu Lys Leu Xaa Lys Lys Leu Leu Lys Lys
1               5                   10
Xaa Lys Lys Leu Leu Lys Lys Leu
15
```

(2) INFORMATION FOR SEQ ID NO:38:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: C-terminal amide, acetylated at
N-terminus.

(xi) SEQUENCE DESCRIPTION:SEQ ID NO:38:

```
Leu Lys Leu Met Lys Lys Leu Leu Lys Lys
1               5                   10
Lys Lys Lys Leu Leu Lys Lys Leu
15
```

(2) INFORMATION FOR SEQ ID NO:39:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: C-terminal amide, acetylated at
N-terminus.

(xi) SEQUENCE DESCRIPTION:SEQ ID NO:39:

```
Leu Lys Leu Lys Lys Lys Leu Leu Lys Lys
1               5                   10
Met Lys Lys Leu Leu Lys Lys Leu
15
```

(2) INFORMATION FOR SEQ ID NO:40:

(i) SEQUENCE CHARACTERISTICS:
(A) LENGTH: 18 amino acids
(B) TYPE: amino acid
(C) STRANDEDNESS:
(D) TOPOLOGY: linear (ii) MOLECULE TYPE: peptide (ix) FEATURE:
(D) OTHER INFORMATION: C-terminal amide, acetylated at
N-terminus, Xaa is methionine
sulfoxide.

(xi) SEQUENCE DESCRIPTION:SEQ ID NO:40:

```
Leu Lys Leu Xaa Lys Lys Leu Leu Lys Lys
1               5                   10
Lys Lys Lys Leu Leu Lys Lys Leu
15
```

(2) INFORMATION FOR SEQ ID NO:41:

( i ) SEQUENCE CHARACTERISTICS:
- ( A ) LENGTH: 18 amino acids
- ( B ) TYPE: amino acid
- ( C ) STRANDEDNESS:
- ( D ) TOPOLOGY: linear ( i i ) MOLECULE TYPE: peptide ( i x ) FEATURE:
- ( D ) OTHER INFORMATION: C-terminal amide, acetylated at N-terminus, Xaa is methionine sulfoxide.

( x i ) SEQUENCE DESCRIPTION:SEQ ID NO:41:

```
Leu Lys Leu Lys Lys Lys Leu Leu Lys Lys
1               5                    10
Xaa Lys Lys Leu Leu Lys Lys Leu
15
```

( 2 ) INFORMATION FOR SEQ ID NO:42:

( i ) SEQUENCE CHARACTERISTICS:
- ( A ) LENGTH: 18 amino acids
- ( B ) TYPE: amino acid
- ( C ) STRANDEDNESS:
- ( D ) TOPOLOGY: linear ( i i ) MOLECULE TYPE: peptide ( i x ) FEATURE:
- ( D ) OTHER INFORMATION: May be a C-terminal amide, may be acetylated at N-terminus.

( x i ) SEQUENCE DESCRIPTION:SEQ ID NO:42:

```
Leu Lys Leu Arg Lys Lys Leu Leu Lys Lys
1               5                    10
Leu Lys Lys Leu Leu Lys Lys Leu
15
```

( 2 ) INFORMATION FOR SEQ ID NO:43:

( i ) SEQUENCE CHARACTERISTICS:
- ( A ) LENGTH: 18 amino acids
- ( B ) TYPE: amino acid
- ( C ) STRANDEDNESS:
- ( D ) TOPOLOGY: linear ( i i ) MOLECULE TYPE: peptide ( i x ) FEATURE:
- ( D ) OTHER INFORMATION: May be a C-terminal amide, may be acetylated at N-terminus.

( x i ) SEQUENCE DESCRIPTION:SEQ ID NO:43:

```
Leu Lys Leu His Lys Lys Leu Leu Lys Lys
1               5                    10
Leu Lys Lys Leu Leu Lys Lys Leu
15
```

( 2 ) INFORMATION FOR SEQ ID NO:44:

( i ) SEQUENCE CHARACTERISTICS:
- ( A ) LENGTH: 18 amino acids
- ( B ) TYPE: amino acid
- ( C ) STRANDEDNESS:
- ( D ) TOPOLOGY: linear ( i i ) MOLECULE TYPE: peptide ( i x ) FEATURE:
- ( D ) OTHER INFORMATION: May be a C-terminal amide, may be acetylated at N-terminus.

( x i ) SEQUENCE DESCRIPTION:SEQ ID NO:44:

```
Leu Lys Leu Leu Lys Lys Leu Leu Lys Lys
1               5                    10
Arg Lys Lys Leu Leu Lys Lys Leu
15
```

( 2 ) INFORMATION FOR SEQ ID NO:45:

( i ) SEQUENCE CHARACTERISTICS:
        ( A ) LENGTH: 18 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: May be a C- terminal amide, may be acetylated at N-terminus.

( x i ) SEQUENCE DESCRIPTION:SEQ ID NO:45:

```
Leu Lys Leu Leu Lys Lys Leu Leu Lys Lys
 1               5                  10
His Lys Lys Leu Leu Lys Lys Leu
15
```

( 2 ) INFORMATION FOR SEQ ID NO:46:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated at N- terminus.

( x i ) SEQUENCE DESCRIPTION:SEQ ID NO:46:

```
Lys Leu Leu Lys Lys Leu Leu Lys Lys Leu
 1               5                  10
Lys Lys Leu Leu Lys Lys Leu
15
```

( 2 ) INFORMATION FOR SEQ ID NO:47:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated at N- terminus.

( x i ) SEQUENCE DESCRIPTION:SEQ ID NO:47:

```
Leu Leu Leu Lys Lys Leu Leu Lys Lys Leu
 1               5                  10
Lys Lys Leu Leu Lys Lys Leu
15
```

( 2 ) INFORMATION FOR SEQ ID NO:48:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated at N- terminus.

( x i ) SEQUENCE DESCRIPTION:SEQ ID NO:48:

```
Leu Lys Leu Lys Lys Leu Leu Lys Lys Leu
 1               5                  10
```

```
            Lys  Lys  Leu  Leu  Lys  Lys  Leu
             15
```

( 2 ) INFORMATION FOR SEQ ID NO:49:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
           at N- terminus.

( x i ) SEQUENCE DESCRIPTION:SEQ ID NO:49:
```
            Leu  Lys  Leu  Leu  Lys  Leu  Leu  Lys  Lys  Leu
             1                  5                         10
            Lys  Lys  Leu  Leu  Lys  Lys  Leu
             15
```

( 2 ) INFORMATION FOR SEQ ID NO:50:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
           at N- terminus.

( x i ) SEQUENCE DESCRIPTION:SEQ ID NO:50:
```
            Leu  Lys  Leu  Leu  Lys  Lys  Leu  Lys  Lys  Leu
             1                  5                         10
            Lys  Lys  Leu  Leu  Lys  Lys  Leu
             15
```

( 2 ) INFORMATION FOR SEQ ID NO:51:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
           at N- terminus.

( x i ) SEQUENCE DESCRIPTION:SEQ ID NO:51:
```
            Leu  Lys  Leu  Leu  Lys  Lys  Leu  Leu  Lys  Leu
             1                  5                         10
            Lys  Lys  Leu  Leu  Lys  Lys  Leu
             15
```

( 2 ) INFORMATION FOR SEQ ID NO:52:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
           at N- terminus.

( x i ) SEQUENCE DESCRIPTION:SEQ ID NO:52:

```
            Leu  Lys  Leu  Leu  Lys  Lys  Leu  Leu  Lys  Lys
            1              5                        10
            Lys  Lys  Leu  Leu  Lys  Lys  Leu
            15
```

( 2 ) INFORMATION FOR SEQ ID NO:53:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
            at N- terminus.

( x i ) SEQUENCE DESCRIPTION:SEQ ID NO:53:
```
            Leu  Lys  Leu  Leu  Lys  Lys  Leu  Leu  Lys  Lys
            1              5                        10
            Leu  Lys  Leu  Leu  Lys  Lys  Leu
            15
```

( 2 ) INFORMATION FOR SEQ ID NO:54:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
            at N- terminus.

( x i ) SEQUENCE DESCRIPTION:SEQ ID NO:54:
```
            Leu  Lys  Leu  Leu  Lys  Lys  Leu  Leu  Lys  Lys
            1              5                        10
            Leu  Lys  Lys  Leu  Lys  Lys  Leu
            15
```

( 2 ) INFORMATION FOR SEQ ID NO:55:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
            at N- terminus.

( x i ) SEQUENCE DESCRIPTION:SEQ ID NO:55:
```
            Leu  Lys  Leu  Leu  Lys  Lys  Leu  Leu  Lys  Lys
            1              5                        10
            Leu  Lys  Lys  Leu  Leu  Lys  Leu
            15
```

( 2 ) INFORMATION FOR SEQ ID NO:56:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: C-terminal amide, acetylated
            at N- terminus.

(x i) SEQUENCE DESCRIPTION:SEQ ID NO:56:

```
Leu Lys Leu Leu Lys Lys Leu Leu Lys Lys
1               5                   10
Leu Lys Lys Leu Leu Lys Leu
15
```

(2) INFORMATION FOR SEQ ID NO:57:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: acetylated at N-terminus, may be a
        C-terminal amide (x i) SEQUENCE DESCRIPTION:SEQ ID NO:57:

```
Leu Lys Lys Leu
1
```

(2) INFORMATION FOR SEQ ID NO:58:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: acetylated at N-terminus, may be a
        C-terminal amide (x i) SEQUENCE DESCRIPTION:SEQ ID NO:58:

```
Leu Lys Lys Leu Leu Lys Lys Leu
1               5
```

(2) INFORMATION FOR SEQ ID NO:59:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: acetylated at N-terminus, may be a
        C-terminal amide (x i) SEQUENCE DESCRIPTION:SEQ ID NO:59:

```
Leu Leu Lys Lys Leu Lys Lys Leu Leu Lys
1               5                   10
Lys Leu
```

(2) INFORMATION FOR SEQ ID NO:60:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (ix) FEATURE:
        (D) OTHER INFORMATION: acetylated at N-terminus, may be a
        C-terminal amide (x i) SEQUENCE DESCRIPTION:SEQ ID NO:60:

```
Leu Lys Lys Leu Leu Lys Leu Leu Lys Lys
```

```
                 1               5                        10
          Leu  Leu  Lys  Lys  Leu  Lys  Lys  Leu  Leu  Lys
          15                        20
          Lys  Leu
```

( 2 ) INFORMATION FOR SEQ ID NO:61:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: acetylated at N-terminus, may be
        a C-terminal amide.

( x i ) SEQUENCE DESCRIPTION:SEQ ID NO:61:
```
          Leu  Lys  Lys  Leu  Leu  Lys  Lys  Leu  Leu  Lys
          1                   5                        10
          Leu  Leu  Lys  Lys  Leu  Leu  Lys  Lys  Leu  Lys
          15                       20
          Lys  Leu  Leu  Lys  Lys  Leu
          25
```

( 2 ) INFORMATION FOR SEQ ID NO:62:

( i ) SEQUENCE CHARACTERISTICS:
        ( A ) LENGTH: 30 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: acetylated at N-terminus, may be
        a C-terminal amide.

( x i ) SEQUENCE DESCRIPTION:SEQ ID NO:62:
```
          Leu  Leu  Lys  Lys  Leu  Lys  Lys  Leu  Leu  Lys
          1                   5                        10
          Lys  Leu  Leu  Lys  Leu  Leu  Lys  Lys  Leu  Leu
          15                       20
          Lys  Lys  Leu  Lys  Lys  Leu  Leu  Lys  Lys  Leu
          25                       30
```

( 2 ) INFORMATION FOR SEQ ID NO:63:

( i ) SEQUENCE CHARACTERISTICS:
        ( A ) LENGTH: 36 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( D ) OTHER INFORMATION: acetylated at N-terminus, may be
        a C- terminatal amide ( x i ) SEQUENCE DESCRIPTION:SEQ ID NO:63:
```
          Leu  Lys  Leu  Leu  Lys  Lys  Leu  Leu  Lys  Lys
          1                   5                        10
          Leu  Lys  Lys  Leu  Leu  Lys  Lys  Leu  Leu  Lys
          15                       20
          Leu  Leu  Lys  Lys  Leu  Leu  Lys  Lys  Leu  Lys
          25                       30
          Lys  Leu  Leu  Lys  Lys  Leu
          35
```

( 2 ) INFORMATION FOR SEQ ID NO:64:

( i ) SEQUENCE CHARACTERISTICS:
        ( A ) LENGTH: 13 amino acids
        ( B ) TYPE: amino acid (C) STRANDEDNESS:
                (D) TOPOLOGY: linear (ii) MOLECULE TYPE: peptide (ix) FEATURE:
                (D) OTHER INFORMATION: C-terminal amide, may be
                    acetylated at N-terminus.

(xi) SEQUENCE DESCRIPTION:SEQ ID NO:64:
                Lys Leu Leu Lys Lys Leu Lys Lys Leu Leu
                 1               5                  10
                Lys Lys Leu (2) INFORMATION FOR SEQ ID NO:65:

(i) SEQUENCE CHARACTERISTICS:
                (A) LENGTH: 14 amino acids
                (B) TYPE: amino acid
                (C) STRANDEDNESS:
                (D) TOPOLOGY: linear (ii) MOLECULE TYPE: peptide (ix) FEATURE:
                (D) OTHER INFORMATION: C-terminal amide, may be
                    acetylated at N-terminus.

(xi) SEQUENCE DESCRIPTION:SEQ ID NO:65:
                Lys Lys Leu Leu Lys Lys Leu Lys Lys Leu
                 1               5                  10
                Leu Lys Lys Leu (2) INFORMATION FOR SEQ ID NO:66:

(i) SEQUENCE CHARACTERISTICS:
                (A) LENGTH: 15 amino acids
                (B) TYPE: amino acid
                (C) STRANDEDNESS:
                (D) TOPOLOGY: linear (ii) MOLECULE TYPE: peptide (ix) FEATURE:
                (D) OTHER INFORMATION: C-terminal amide, may be
                    acetylated at N-terminus.

(xi) SEQUENCE DESCRIPTION:SEQ ID NO:66:
                Leu Lys Lys Leu Leu Lys Lys Leu Lys Lys
                 1               5                  10
                Leu Leu Lys Lys Leu
                 15

(2) INFORMATION FOR SEQ ID NO:67:

(i) SEQUENCE CHARACTERISTICS:
                (A) LENGTH: 11 amino acids
                (B) TYPE: amino acid
                (C) STRANDEDNESS:
                (D) TOPOLOGY: linear (ii) MOLECULE TYPE: peptide (ix) FEATURE:
                (D) OTHER INFORMATION: C-terminal amide, may be
                    acetylated at N-terminus.

(xi) SEQUENCE DESCRIPTION:SEQ ID NO:67:
                Leu Lys Lys Leu Lys Lys Leu Leu Lys Lys
                 1               5                  10
                Leu (2) INFORMATION FOR SEQ ID NO:68:

(i) SEQUENCE CHARACTERISTICS:
                (A) LENGTH: 18 amino acids
                (B) TYPE: amino acids
                (C) STRANDEDNESS:

(D) TOPOLOGY: linear (ii) FEATURE:
(D) OTHER INFORMATION: C-terminal amide, may be acetylated at N-terminus.

(xi) SEQUENCE DESCRIPTION:SEQ ID NO: 68:
Leu Lys Leu Leu Lys Lys Leu Leu Lys Lys
1               5                       10
Gly Lys Lys Leu Leu Lys Lys Leu
        15

AMPHIPHILIC PEPTIDE COMPOSITIONS AND ANALOGUES THEREOF

This invention was made with government support under Contract No. DIR 8713707 awarded by the National Science Foundation. The government has certain rights in the invention.

This application is a continuation-in-part of application Ser. No. 554,422, filed Jul. 9, 1990 and now abandoned.

This invention relates to biologically active amphiphilic peptides. More particularly, this application relates to biologically active amphiphilic peptides useful in pharmaceutical compositions and to analogues of a biologically active amphiphilic peptide wherein at least one amino acid residue in the peptide has been substituted with another amino acid residue, with said analogues being commonly referred to as "substitution analogues."

In accordance with an aspect of the present invention, there is provided a process for inhibiting growth of a target organism such as a cell or virus which comprises administering to a host a biologically active amphiphilic peptide of the following structural formula:

$$R_1-R_1-R_2-R_1-R_1-R_2-R_2-R_1-R_1-R_2-R_2-R_1-R_2-R_2,$$

wherein $R_1$ is a hydrophobic amino acid, and $R_2$ is a basic hydrophilic or neutral hydrophilic amino acid. The peptide is administered to the host in an amount effective to inhibit growth of a target cell or virus.

The hydrophobic amino acids are selected from the group consisting of Ala, Cys, Phe, Gly, Ile, Leu, Met, methionine sulfoxide, Val, Trp, and Tyr.

The basic hydrophilic amino acids are selected from the group consisting of Lys, Arg, His, orn, homoarginine (Har), 2,4-diaminobutyric acid (Dbu), and p-aminophenylalanine.

The neutral hydrophilic amino acids are selected from the group consisting of Asn, Gln, Ser, and Thr.

In accordance with one embodiment, $R_1$ is leucine. In accordance with another embodiment, $R_2$ is lysine.

In a preferred embodiment, the peptide is of the following structure (I):

I. LeuLeuLysLeuLeuLysLysLeuLeuLysLysLeuLysLys
            5                    10
(SEQ ID NO: 1)

In accordance with another aspect of the present invention, there is provided a process for inhibiting growth of a target organism such as a cell or virus which comprises administering to a host a biologically active amphiphilic peptide of the following structural formula:

$$R_2-R_1-R_1-R_2-R_2-R_1-R_2-R_2-R_1-R_1-R_2-R_2-R_1-R_1,$$

wherein $R_1$ and $R_2$ are as hereinabove described. The peptide is administered to the host in an amount effective to inhibit the growth of a target cell or virus.

In a preferred embodiment, the peptide is of the following structure (II):

II. LysLeuLeuLysLysLeuLysLysLeuLeuLysLysLeuLeu
            5                    10
(SEQ ID NO: 2)

Peptides I and II are further described in Houghten, et al., *BioChromatography*, Vol. 2, No. 2, pgs. 80–83 (1987).

Most preferably, Peptides I and II are acetylated with a $CH_3CO$-group at the N-terminus, said $CH_3CO$-group being hereinafter indicated by the letter X.

In accordance with yet another aspect of the present invention, there is provided a biologically active amphiphilic peptide of the following structural formula: $R_1-R_2-R_1-R_1-R_2-R_2-R_1-R_1-R_2-R_2-R_1-R_2-R_2-R_1R_1-R_2-R_2-R_1$, wherein $R_1$ is a hydrophobic amino acid, and $R_2$ is a basic hydrophilic or neutral hydrophilic amino acid as before defined.

Preferably, the peptide is acetylated with a $CH_3CO$-group at the N-terminal, said $CH_3CO$-group being represented herein by the letter X as hereinabove described.

Most preferably, the peptide is of the following structure (III), and acetylated at the N-terminus:

III. X—LeuLysLeuLeuLysLysLeuLeuLysLysLeuLysLys
              5                    10
LeuLeuLysLysLeu
15
(SEQ ID NO: 3)

In accordance with another aspect of the present invention, there is provided a compound comprising an analogue of Peptide III, said peptide being in an amide- or carboxy-terminated (preferably amide-terminated) form. The Peptide III, also hereinafter sometimes referred to as the "parent peptide", is represented by the following structural formula, and the numbers below each amino acid residue refer to the position of the residue in the peptide.

LeuLysLeuLeuLysLysLeuLeuLysLysLeuLysLysLeuLeuLysLysLeu
1  2  3  4  5  6  7  8  9  10 11 12 13 14 15 16 17 18
(SEQ ID NO: 3)

The parent peptide is substituted in at least one of positions 1, 3, 4 and 7–18 as follows:

| Residue No. | Substituent |
|---|---|
| 1 | Methionine sulfoxide, Lys, or Met |
| 3 | Methionine sulfoxide, Lys, or Met |
| 4 | Methionine sulfoxide, Lys, Met, His, Ser, or Arg |
| 7 | Methionine sulfoxide, Lys, or Met |
| 8 | Methionine sulfoxide, Lys, or Met |
| 9 | Methionine sulfoxide |
| 10 | Methionine sulfoxide |
| 11 | Methionine sulfoxide, Met, Ser, Lys, Arg, His or Gly |
| 12 | Methionine sulfoxide |
| 13 | Methionine sulfoxide, or Met |
| 14 | Methionine sulfoxide, Lys, or Met |
| 15 | Methionine sulfoxide, Lys, or Met |
| 16 | Methionine sulfoxide |
| 17 | Methionine sulfoxide |
| 18 | Methionine sulfoxide, or Met |

In accordance with one embodiment, at least one of amino acid residues 1, 7, 8, 11, 14, 15, and 18 can be substituted with methionine sulfoxide.

In accordance with another embodiment, at least one of amino acid residues 1, 7, 8, 14, 15, and 18 can be substituted with a methionine residue.

In accordance with yet another embodiment, at least one of amino acid residues 4, 7, 8, 11, and 14 can be substituted with a lysine residue.

In accordance with a further embodiment, amino acid residue 4 is substituted with a lysine residue, and amino acid residue 11 is substituted with a methionine In accordance with another embodiment, at least one of amino acid residues 4 and 11 can be substituted with an arginine residue.

In accordance with yet another embodiment, at least one of amino acid residues 4 and 11 can be substituted with a histidine residue.

In accordance with another embodiment, amino acid residue 11 is substituted with a glycine residue.

Applicants have found that when employing the substitution analogues of the parent peptide having the structural formula hereinabove described, such peptides display biological activity about equal to or greater than the parent. Such peptides are referred to as "successful substitution analogues".

As used herein, the term "substitution analogue" includes the parent peptide having the structural formula hereinabove described in which at least one amino acid residue of the peptide structure has been substituted with a different amino acid residue.

In accordance with another aspect of the present invention, there is provided a compound comprising an analogue of the parent peptide hereinabove described, said peptide being in an amide- or carboxy-terminated (preferably amide-terminated) form, wherein at least one of the amino acid residues 1 through 7, 9, 11, 12, 14, 16 or 18 is deleted from the parent peptide. In one embodiment, at least one of amino acid residues 3, 7, 11, 14 or 18 is deleted from the parent peptide. In other embodiments, amino acid residues 1 through 3, 1 through 4, 1 through 5, 1 through 6, and 1 through 7 are deleted from the peptide.

Applicants have found that when employing the deletion analogues of the parent peptide having the structural formula hereinabove described, such peptides display biological activity equal to or greater than the parent. Such peptides are referred to as "successful deletion analogues".

As used herein, the term "deletion analogue" includes the parent peptide having the structural formula hereinabove described in which at least one of the amino acid residues of the peptide structure has been deleted from the peptide.

In accordance with a further aspect of the present invention, there is provided a biologically active amphiphilic peptide which includes the following structural formula $Y_{10}$:

$$R_1-R_1-R_2-R_2-R_1-R_2-R_2-R_2-R_1-R_2-R_2-R_1-R_1,$$

wherein $R_1$ and $R_2$ are as hereinabove described.

In one embodiment, the peptide can include the following structure:

$Y_{10}-Z_{10}$, wherein $Y_{10}$ is as hereinabove described, and $Z_{10}$ is:

(i) $R_2$;
(ii) $R_2-R_1$; or
(iii) $R_2-R_1-R_1$.

In one embodiment, the peptide has the following structural formula:

LeuLeuLysLysLeuLysLysLeuLeuLysLysLeuLeuLysLeuLeu
　　　　　5　　　　　　　10　　　　　　　15
(SEQ ID NO: 4)

The peptides hereinabove described may be acetylated with a $CH_3CO$-group at the N-terminal, said $CH_3CO$-group being indicated by the letter X as described herein.

The use of the hereinabove described peptides, which also includes Peptide III having substitution(s), or deletion(s) of amino acid residues, in accordance with the present invention, is effective as an antibiotic, and can be employed to inhibit, prevent or destroy the growth or proliferation of microbes, such as bacteria, fungi, viruses, or the like. Similarly, such compounds can be employed as an anti-viral composition to inhibit, prevent or destroy the growth or proliferation of viruses.

Such peptides can also be employed as a spermicide to inhibit, prevent or destroy the motility of sperm.

Such peptides can also be employed as anti-tumor agents to inhibit the growth of or destroy tumors, including cancer cells.

The peptides can also be employed as anti-parasitic agents to inhibit the growth of proliferation of or destroy parasites.

The peptides have a broad range of potent antibiotic activity against a plurality of microorganisms (target organisms), including Gram-positive and Gram-negative bacteria, fungi, protozoa, parasites and the like. Such compounds can be employed for treating or controlling microbial infection caused by organisms which are sensitive to such compounds.

The peptide of the present invention can also be employed in promoting or stimulating healing of a wound in a host.

The term "wound healing" as used herein includes various aspects of the would healing process. These aspects include, but are not limited to, increased contraction of the wound, increased deposition of connective tissue, as evidenced by, for example, increased deposition of collagen in the wound, and increased tensile strength of the wound; i.e., the peptides increase wound breaking strength. The peptides of the present invention can also be employed so as to reverse the inhibition of wound healing caused by a depressed or compromised immune system.

The compositions of the present invention can also be used in the treatment of external burns and to treat and/or prevent skin and burn infections. In particular, the compositions may be used to treat skin and burn infections caused by organisms such as, but not limited to, P.aeruginosa and S.aureus.

The peptides of the present invention can be used in the treatment of external burns and to treat and/or prevent skin and burn infections. In particular, the peptides can be used to treat skin and burn infections cause by organisms such as, but not limited to, P. aeruginosa and S. aureus.

The peptides are also useful in the prevention or treatment of eye infections. Such infections can be caused by bacteria such as, but not limited to, P. aeruginosa, S. aureus, and N. gonorrhoeae, by fungi such as but not limited to C. albicans and A. fumigatus, by parasites such as but not limited to A. castellani, or by viruses.

The peptides can also be effective in killing cysts, spores, or trophozoites of infection-causing organisms. Such organisms include, but are not limited to Acanthamoeba which forms trophozoites or cysts, C. albicans, which forms spores, and A. fumigatus, which forms spores as well.

The peptides can also be used as preservatives or sterilants for materials susceptible to microbial contamination. In vitro activity against bacteria is exemplified hereinafter in Examples 3-9 and 11-12.

The peptides can also be administered to plants in order to inhibit or destroy the growth or proliferation of plant pathogen target organisms such as microbes, bacteria, viruses, or parasites, fungi, cysts, or spores.

The peptides of the present invention can be administered to a target cell or host by direct or indirect application. For example, the peptide may be administered topically or systemically.

The peptides of the present invention can be administered to a host in particular an animal, in an effective antibiotic and/or anti-tumor and/or anti-viral and/or anti-parasitic and/or anti-microbial and/or a spermicidal amount; i.e., a growth inhibiting amount.

In general, the peptide is administered in a dosage of from about 0.1 mg to about 500 mg per kilogram of body weight, when administered systemically. When administered topically, the peptide is used in a concentration of from about 0.05 percent to about 5 percent.

The peptides, in accordance with the present invention, can be employed for treating a wide variety of hosts. In accordance with a preferred embodiment, a host can be an animal, and such animal can be a human or non-human animal.

The peptides can be employed in a wide variety of pharmaceutical compositions such as, but not limited to, those described in *Remington's Pharmaceutical Sciences*, 16th edition, A.Osol, ed., Mack Publishing Company, Easton, Pa. (1980), in combination With a non-toxic pharmaceutical carrier or vehicle such as a filler, non-toxic buffer, or physiological saline solution. Such pharmaceutical compositions can be used topically or systemically and can be in any suitable form such as a liquid, solid, semi-solid, injectable solutions, tablet, ointment, lotion, paste, capsule or the like. Such peptides can also be used in combination with adjuvants, protease inhibitors, or compatible drugs where such a combination is seen to be desirable or advantageous in controlling infection caused by harmful microorganisms including protozoa, viruses, parasites, and the like.

The peptides, whether substituted or unsubstituted, of the present invention, (both amide- and carboxy-terminated) can be synthesized by any convenient method of peptide synthesis as are well-known to skilled workers. Solid phase synthesis methods are particularly preferred.

Although the scope of the present invention is not intended to be limited to any theoretical reasoning, the peptides may be induced into an amphipathic -helical configuration, which is reported to be an element responsible for the activity of known antimicrobial peptides.

The peptides described herein were prepared by the method of simultaneous multiple peptide synthesis (SMPS). This method is described in detail in Houghten, "General Method for the Rapid Solid-Phase Synthesis of Large Numbers of Peptides; Specificity of Antigen-Antibody Interaction at the Level of Individual Amino Acids," *Proc. Natl. Acad. Sci., U.S.A.*, Vol. 82, pgs. 5131-5135 (1985), in Houghten et al. "Simultaneous Multiple Peptide Synthesis; The Rapid Preparation of Large Numbers of Discrete Peptides for Biological, Immunological, and Methodological Studies", *Peptide Chemistry*, pgs. 295-298 (1987), and in U.S. Pat. No. 4,631,211, which is hereby incorporated by reference.

The peptides can also be synthesized through genetic engineering techniques. Thus, it is contemplated that within the scope of the present invention, there may be provided DNA which encodes any of the hereinabove described peptides, and it is contemplated that the peptides may be administered to a host by administering DNA which encodes one of the hereinabove described peptides.

It is also contemplated within the scope of the present invention to provide a plant which is genetically engineered with DNA which encodes one of the hereinabove described peptides, whereby such peptide is expressed by the plant.

For purposes of the following examples, substitution analogues of the parent peptide hereinabove described were prepared wherein various amino acid residues were substituted.

For purposes of comparison, a complete parent peptide of the structure hereinabove described can also be prepared by the SMPS method.

The invention will now be described with respect to the following examples; however, the scope of th present invention is not intended to be limited thereby.

EXAMPLE 1—PEPTIDE SYNTHESIS

Peptide synthesis of the parent peptide (SEQ ID NO:3) hereinabove described and its substitution and deletion analogues, and of Peptide I (SEQ ID NO:1) as hereinabove described, was accomplished by using the strategy of simultaneous multiple peptide synthesis. All solvents and reagents were of analytical grade and were used without further purification. Standard N-t-Boc-protected amino acids were employed in the synthesis. The side chain functionalities used were benzyl (Ser) when serine is employed in the peptide structure, 2-Cl-Z (Lys)(Z=benzyloxycarbonyl), $N^{im}$-DNP (His) when histidine is included in the peptide structure, and sulfoxide (Met). Peptide synthesis was performed beginning with 100 mg of either Boc-amino acids-Pam resin to produce C-terminal carboxyl peptide (Pam purchased from Applied Biosystems, substitution 0.56 meq/gm in an amino acyl-4-[oxymethyl]phenylacetic acid derivative of amino polystyrene) or methylbenzhydrylamine (MBHA) resin (substitution-0.65 meq/gm) per resin packet to produce C-terminal amide peptide.

After removing the final Boc-group and neutralizing the salt of the α-amino group, N-acetylation is carried out in the same manner as a coupling step. Instead of an amino acid, 0.3M acetylimidazole ($C_3H_6N_2O$) in methylene chloride ($CH_2Cl_2$) is reacted with the free N-terminal group without adding any activator.

After synthesis, completely protected peptide resins were treated three times with 0.5M thiophenol in DMF to remove the Nim- dinitrophenyl group from Histidine when histidine is included in the peptide structure. The final Boc-group was removed with TFA to avoid t-butylation of methionyl residues during final HF treatment when methionine is included in the peptide structure. Cleavage was performed using the Low-High HF procedure. When methionine is part of the peptide structure, one may elect not to cleave the sulfoxide group from the methionine residue(s), thus resulting in a peptide which includes methionine sulfoxide residue(s). Tam et al., *J. Am. Chem. Soc.* Vol. 105, p. 6442 (1983). For peptides synthesized on Pam resin, the low-HF was carried out without removing the resin from the packet, using a multiple vessel HF apparatus for two hours at 0° C. For peptides prepared using MBHA resin, the low HF procedure was performed in a common reaction vessel for two hours at 0° C. For Pam resin peptides, the low-HF mixture was evacuated from the 24 individual reaction vessels by a water aspirator followed by a mechanical pump. The low-HF reaction vessel containing the bags with MBHA resin was emptied of the low-HF mixture by pouring off the liquid into a waste container. The bags were washed immediately with cold ether followed by alternating washes of CH$_3$Cl$_2$, DMF, CH$_2$Cl$_2$, IPA, CH$_3$Cl$_2$. The packets were then dried and put into individual tubes of the 24 vessel HF apparatus with 0.7 ml of anisole as scavenger. The high-HF was performed by condensing dry hydrogen fluoride at −70° C. The reaction took place at −10° C. for one hour and −5° C.-0° C. for the last 30 minutes. HF was evaporated using a strong flow of nitrogen. Finally, residual carbonium ion scavengers were removed by washing with dry ether.

The crude peptides were subsequently extracted with 10 percent acetic acid and subjected to RP-HPLC on an analytical reversed phase column (Vidac ODS 25 cm×4.6 mm), using a Beckman-Altek Model 421 HPLC system and two model 110A pumps. The solvent system was composed of buffer A, 0.05 percent TFA/H$_2$O, and buffer B, 0.05 percent TFA/CH3CN with a flow rate of 1.0 ml/min. The peptides were detected at 215 nm using a Hitachi 100-20 spectrophotometer.

Purification of the peptides was accomplished by reverse-phase HPLC on a Vidac C18 (22 mm×25cm), 10 μm packing column with an eluting gradient composed of CH3CN and 0.05 percent TFA. Amino acid analysis was carried out on a Beckman 6300 analyzer following hydrolysis of the peptides in constant (boiling) 6N HCl at 110° C. for 24 hours, and such analysis was within ±10 percent of theory.

EXAMPLE 2—ANTIMICROBIAL ASSAYS AND HEMOLYTIC ACTIVITY

For the following Examples 3-9, antimicrobial assays were carried out in 96-well tissue culture plates. Each well was incubated with a given microorganism (*Escherichia coli*, *Staphylococcus epidermidis*, or *Pseudomonas aeruginosa*) suspended in LB medium. Upon the addition of the parent peptide having the structural formula hereinabove described, or its substitution analogues, or of Peptide I (dissolved in 1 X PBS, pH 7.0) each well contained a final cell density of 1.0×10$^6$ colony forming units (CFU)/ml. The final peptide concentrations ranged from 1.5 μg/ml to greater than 100 μg/ml.

Addition of peptides to the wells was defined as time zero. At twenty hours, the plates were placed in a Titertek Multiskan apparatus and the O.D.620 determined. The plates as well as the initial innoculum were incubated at 37° C.

Five wells per plate contained media alone, while five others contained medium plus cells. These controls were used to eliminate the possibility of media contamination while providing a measure of uninhibited growth of the microorganisms.

The degree of peptide activity was determined by comparing the substitution analogues with uninhibited growth of the control cells over a twenty-hour period. The effective growth inhibition of the substitution analogues is listed in the examples and tables below.

The hemolytic activity of the parent peptide and its substitution analogues and of Peptide I was examined with human red blood cells. Ten μl of blood were suspended in isotonic PBS buffer (pH 7) to reach a concentration of 2 percent of cells in PBS, followed by the addition of the peptide to reach a final volume of 1 ml. The peptide concentration is 100 μg/ml. The suspension was gently mixed and then incubated for 30 minutes at 37° C. The samples were centrifuged at 1000 g for five minutes. The supernatant was separated from the pellet and the optical density was measured at 414 nm. 100 Percent hemolysis was determined by disrupting the human erythrocytes in pure H$_2$O.

EXAMPLE 3—PARENT PEPTIDE AND ANALOGUES WITH METHIONINE SULFOXIDE SUBSTITUTIONS

A parent peptide having the following structural formula:

X-(SEQ ID NO:3)-NH$_2$ as hereinabove described and analogues thereof wherein a methionine sulfoxide residue was substituted for various amino acid residues of the parent peptide were prepared as hereinabove described in Example 1 and tested for minimum inhibitory concentration with respect to *E. coli*, *P. aeruginosa*, and *S. epidermidis* at a concentration given in μg/ml, and for percent hemolysis of human red blood cells as hereinabove described in Example 2. The minimum inhibitory concentration and percent hemolysis (at a concentration of 100 μg/ml) are listed below in Table I. As used herein, the heading "Amino Acid Residue Substituted" refers to the number of the amino acid residue in the peptide which is substituted with a desired amino acid residue. All other residues remain the same as that of the normal peptide sequence. The term "Minimum Inhibitory Concentration" (MIC) as used herein indicates the minimum concentration of peptide in μg/ml needed to achieve 100 percent effective growth inhibition of the organism.

TABLE I

| Amino Acid Residue Substituted | Minimum Inhibitory Concentration (μg/ml) | | | Percent Hemolysis |
|---|---|---|---|---|
| | E. Coli | P. Aeruginosa | S. epidermidis | |
| None (parent) | 10 | 75 | 2.5 | 6.0 |
| 1 (SEQ ID NO: 5) | 5 | 30 | 10 | 0.4 |
| 2 (SEQ ID NO: 6) | 10 | 40 | 20 | 67.6 |
| 3 (SEQ ID NO: 7) | 10 | 30 | 5 | 3.3 |
| 4 (SEQ ID NO: 8) | 10 | 30 | 5 | 0.3 |
| 5 (SEQ ID NO: 9) | 10 | 10 | 10 | 12.2 |
| 6 (SEQ ID NO: 10) | 10 | 30 | 10 | 12.4 |
| 7 (SEQ ID NO: 11) | 5 | 5 | 10 | 3.7 |
| 8 (SEQ ID NO: 12) | 5 | 10 | 5 | 5.2 |
| 9 (SEQ ID NO: 13) | 10 | 20 | 10 | 5.4 |
| 10 (SEQ ID NO: 14) | 10 | 30 | 10 | 9.7 |
| 11 (SEQ ID NO: 15) | 10 | 5 | 10 | 0.1 |
| 12 (SEQ ID NO: 16) | 10 | 20 | 10 | 9.4 |
| 13 (SEQ ID NO: 17) | 10 | 30 | 10 | 2.4 |
| 14 (SEQ ID NO: 18) | 5 | 5 | 5 | 2.2 |
| 15 (SEQ ID NO: 19) | 5 | 10 | 5 | 4.2 |
| 16 (SEQ ID NO: 20) | 10 | 10 | 20 | 5.8 |
| 17 (SEQ ID NO: 21) | 10 | 30 | 20 | 8.7 |
| 18 (SEQ ID NO: 22) | 5 | 10 | 10 | 7.1 |

EXAMPLE 4—ANALOGUES WITH LYSINE SUBSTITUTIONS

Analogues of the parent peptide described in Example 3 were prepared as hereinabove described in Example 1, wherein a lysine residue was substituted for various amino acid residues. The analogues were then tested for MIC with respect to *E. coli, P. aeruginosa*, and *S. epidermidis*, and for hemolytic activity as hereinabove described in Example 2. The MIC and hemolytic activity is listed below in Table II.

TABLE II

| Amino Acid Residue Substituted | Min. Inhibitory Concentration (μg/ml) | | | |
|---|---|---|---|---|
| | E. Coli | P. Aeruginosa | S. epidermidis | % Hemolysis |
| 1 (SEQ ID NO: 23) | 5 | 30 | 25 | 4.5 |
| 3 (SEQ ID NO: 24) | 5 | 30 | 10 | 5.3 |
| 4 (SEQ ID NO: 25) | 2.5 | 30 | 5 | 4.0 |
| 7 (SEQ ID NO: 26) | 5 | 30 | 5 | 3.1 |
| 8 (SEQ ID NO: 27) | 5 | 20 | 10 | 5.5 |
| 11 (SEQ ID NO: 28) | 5 | 30 | 5 | 3.2 |
| 14 (SEQ ID NO: 29) | 5 | 20 | 10 | 6.1 |
| 15 (SEQ ID NO: 30) | 10 | 20 | 5 | 9.6 |
| 18 (SEQ ID NO: 31) | 10 | 20 | 10 | 16.8 |

EXAMPLE 5—ANALOGUES WITH METHIONINE SUBSTITUTIONS

Analogues with methionine substitutions

Analogues of the parent peptide described in Example 3 were prepared as described in Example 1, wherein a methionine residue was substituted for various amino acid residues. The analogues were then tested for MIC with respect to *E. coli, P. aeruginosa*, and *S. epidermidis*, and for hemolytic activity as hereinabove described in Example 2. The MIC and hemolytic activity is listed below in Table III.

TABLE III

| Amino Acid Residue Substituted | Min. Inhibitory Concentration (μg/ml) | | | |
|---|---|---|---|---|
| | E. Coli | P. Aeruginosa | S. epidermidis | % Hemolysis |
| 1 (SEQ ID NO: 5) | 5 | 20 | 5 | 6.3 |
| 2 (SEQ ID NO: 6) | 10 | 40 | 10 | 15.0 |
| 3 (SEQ ID NO: 7) | 20 | 30 | 20 | 4.4 |
| 4 (SEQ ID NO: 8) | 10 | 20 | 10 | 5.3 |
| 5 (SEQ ID NO: 9) | 30 | 40 | 20 | 20.0 |
| 6 (SEQ ID NO: 10) | 10 | 30 | 10 | 26.8 |
| 7 (SEQ ID NO: 11) | 5 | 10 | 10 | 8.2 |
| 8 (SEQ ID NO: 12) | 5 | 30 | 10 | 8.1 |
| 9 (SEQ ID NO: 13) | 10 | 30 | 10 | 18.1 |
| 10 (SEQ ID NO: 14) | 10 | 30 | 10 | 39.6 |
| 11 (SEQ ID NO: 15) | 10 | 30 | 10 | 9.2 |
| 12 (SEQ ID NO: 16) | 10 | 30 | 20 | 53.2 |
| 13 (SEQ ID NO: 17) | 10 | 30 | 10 | 7.1 |
| 14 (SEQ ID NO: 18) | 5 | 30 | 5 | 9.7 |
| 15 (SEQ ID NO: 19) | 5 | 30 | 5 | 8.4 |
| 16 (SEQ ID NO: 20) | 10 | 50 | 10 | 13.7 |
| 17 (SEQ ID NO: 21) | 20 | 30 | 20 | 13.9 |
| 18 (SEQ ID NO: 22) | 5 | 20 | 10 | 5.5 |

EXAMPLE 6—ANALOGUES WITH SUBSTITUTIONS AT AMINO ACID RESIDUES 4 AND 11

Analogues of the parent peptide of Example 3 were prepared as described in Example 1, wherein amino acid residues 4 and 11 were substituted with lysine, arginine, histidine, serine, methionine or methionine sulfoxide residues. The structures of these analogues were as follows:

| Analogue No. | Structure |
|---|---|
| 1 | X(SEQ ID NO: 32) —NH$_2$ |
| 2 | X(SEQ ID NO: 33) —NH$_2$ |
| 3 | X(SEQ ID NO: 34) —NH$_2$ |
| 4 | X(SEQ ID NO: 35) —NH$_2$ |
| 5 | X(SEQ ID NO: 36) —NH$_2$ |
| 6 | X(SEQ ID NO: 37) —NH$_2$ |
| 7 | X(SEQ ID NO: 38) —NH$_2$ |
| 8 | X(SEQ ID NO: 39) —NH$_2$ |
| 9 | X(SEQ ID NO: 40) —NH$_2$ |
| 10 | X(SEQ ID NO: 41) —NH$_2$ |

The analogues were then tested for MIC with respect to *E. coli, P. aeruginosa*, and *S. epidermidis*, and for hemolytic activity as described in Example 2. The results for each analogue are given in Table IV below:

TABLE IV

| Analogue No. | Min. Inhibitory Concentration (μg/ml) | | | |
|---|---|---|---|---|
| | E. Coli | P. Aeruginosa | S. epidermidis | % Hemolysis |
| 1 | >100 | 50 | 100 | 0.0 |
| 2 | >100 | >100 | 25 | 0.0 |
| 3 | 25 | 25 | 25 | 0.1 |
| 4 | 25 | 25 | 10 | 0.0 |
| 5 | 10 | 10 | 5 | 3.2 |
| 6 | 100 | 100 | 100 | N/A |
| 7 | 10 | 25 | 5 | 0.0 |
| 8 | 5 | 5 | 5 | 0.9 |
| 9 | 100 | 50 | >100 | N/A |
| 10 | 100 | 100 | 100 | N/A |

EXAMPLE 7—ANALOGUES WITH ARGININE OR HISTIDINE SUBSTITUTIONS

Analogues of the parent peptide described in Example 3 were prepared according to Example 1 wherein arginine or histidine substitutions were made for amino acid residues 4 or 11. The analogues which were prepared are as follows:

| Analogue No. | Amino Acid Residue Substituted | Substituent |
|---|---|---|
| 1 (SEQ ID NO: 42) | 4 | Arginine |
| 2 (SEQ ID NO: 43) | 4 | Histidine |
| 3 (SEQ ID NO: 44) | 11 | Arginine |
| 4 (SEQ ID NO: 45) | 11 | Histidine |

The analogues were then tested for MIC with respect to *E. coil, P. aeruginosa*, and *S. epidermidis*, and for hemolytic activity as described in Example 2. The results are given in Table V below.

TABLE V

| Analogue No. | Min. Inhibitory Concentration (μg/ml) | | | |
|---|---|---|---|---|
| | E. Coli | P. Aeruginosa | S. epidermidis | % Hemolysis |
| 1 | 5 | 5 | 2.5 | 3.0 |
| 2 | 5 | 10 | 2.5 | 2.1 |
| 3 | 10 | 5 | 2.5 | 0.3 |
| 4 | 5 | 1.5 | 1.5 | 2.5 |

EXAMPLE 8

Analogues of the parent peptide of Example 3 were prepared as described in Example 1, wherein either amino acid residue 4, 7, or 11 Was substituted with a methionine sulfoxide residue. The substitution analogues were then processed further to produce fractions of each substitution analogue containing varying proportions of L-methionine-L-sulfoxide residues and L-methionine-D-sulfoxide residues. For purposes of explanation, the terms under the "Proportion" column in Table VI indicate that a certain percentage of the peptide included an L-methionine-L-sulfoxide residue or an L-methionine-D-sulfoxide residue, and an enumerated percentage of the peptides included the other of the L-methionine-L-sulfoxide and L-methionine-D-sulfoxide residue. It has not been determined which percentage corresponds to the L-methionine-L-sulfoxide residue and which percentage corresponds to the L-methionine-D-sulfoxide residue. The analogue preparations were then tested for MIC with respect to E.coli, P. aeruginosa, and S. epidermidis, and for hemolytic activity as described in Example 2. The results are given in Table VI below.

TABLE VI

| Amino Acid Residue Substituted | Pro- portion | Min. Inhibitory Concentration (µg/ml) | | | % Hemo- lysis |
|---|---|---|---|---|---|
| | | E. Coli | P. Aeru- ginosa | S. epide- midia | |
| 4 (SEQ ID NO: 8) | 50/50 | 10 | 5 | 5 | 0.0 |
| 4 (SEQ ID NO: 8) | 60/40 | >10 | 5 | 5 | 0.1 |
| 4 (SEQ ID NO: 8) | 0/100 | >10 | 5 | 5 | 0.5 |
| 4 (SEQ ID NO: 8) | 100/0 | >10 | >5 | >10 | 1.2 |
| 7 (SEQ ID NO: 11) | 70/30 | 10 | >5 | >10 | 0.9 |
| 7 (SEQ ID NO: 11) | 20/80 | 5 | >5 | >10 | 1.1 |
| 7 (SEQ ID NO: 11) | 0/100 | 5 | 2.5 | 5 | 1.8 |
| 11 (SEQ ID NO: 15) | 100/0 | >10 | 2.5 | 2.5 | 0.0 |
| 11 (SEQ ID NO: 15) | 70/30 | 10 | 2.5 | 2 | 0.0 |
| 11 (SEQ ID NO: 15) | 20/80 | 10 | 5 | 2.5 | 0.0 |
| 11 (SEQ ID NO: 15) | 0/100 | 10 | 5 | 5 | 0.2 |

EXAMPLE 9

Peptide I of the following structural formula:

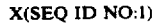

X(SEQ ID NO:1)

was prepared as described in Example 1 and assayed for Minimum Inhibitory Concentration against E.coli and P.aeruginosa and for hemolytic activity as described in Example 2. The Minimum Inhibitory Concentration of Peptide I was 10 µg/ml against E.coli and 5 µg/ml against P.aeruginosa. Hemolytic activity of Peptide I at a concentration of 100 µg/ml was 25.8 percent.

EXAMPLE 10—ANTIMICROBIAL ASSAYS FOR DELETION ANALOGUES

For the deletion analogues of the parent peptide further described in Examples 11 and 12, antimicrobial assays were carried out in 96-well tissue culture plates. Each well was incubated with a given microorganism (Escherichia coli, Staphylococcus epidermidis, Pseudomonas aeruginosa, or Staphylococcus aureus) suspended in LB medium. Upon addition of the parent peptide or its deletion analogues (dissolved in 1×PBS<pH7.0), each well contained a final cell density of $1.3 \times 10^5$ colony forming units (CFU)/ml of E. coli, or $3.5 \times 10^5$ CFU/ml P.aeruginosa, or $3.9 \times 10^5$ CFU/ml S. Aureus or $3.0 \times 10^5$ CFU/ml S. epidermidis. The final peptide concentrations ranged from 1.5 µg/ml to greater than 100 µg/ml.

Addition of peptide to the wells was defined as time zero. At twenty hours, the plates were placed in a Titer- tek Multiskan apparatus and the O.D. 620 determined. The plates as well as the initial innoculum were incubated at 37° C.

Five wells per plate contained medium alone, whereas five others contained medium plus cells. These controls were used to eliminate the possibility of medium contamination, while providing a measure of uninhibited growth of the microorganisms. The degree of peptide activity was determined by comparing the deletion analogues with uninhibited growth of the control cells over a twenty-hour period. The effective growth inhibition of the deletion analogues is listed in the examples and tables below.

EXAMPLE 11—PARENT PEPTIDE AND DELETION ANALOGUES

A parent peptide having the following structural formula: X-(SEQ ID NO:3)-NH₂ as hereinabove described and deletion analogues thereof wherein one of the amino acid residues was deleted were prepared as hereinabove described in Example 1 and tested for minimum inhibitory concentration with respect to E.coli, P.aeruginosa, S.aureus, and S.epidermidis at a concentration given in mg/ml as hereinabove described in Example 9. The minimum inhibitory concentrations are listed below in Table VII. As used herein, the heading "Amino Acid Residue Deleted" refers to the number of the amino acid residue in the peptide which is deleted. All other residues remain the same as that of the normal peptide sequence.

TABLE VII

| Amino Acid Residue Deleted | Minimum Inhibitory Concentration (µg/ml) | | | |
|---|---|---|---|---|
| | E. coli | P. Aerugi- nosa | S. epider- midis | S. aureus |
| None (SEQ ID NO: 3) (parent) | 10 | 75 | 2.5 | 128 |
| 1 (X(SEQ ID NO: 46) —NH₂) | 16 | 16–32 | 4 | 32 |
| 2 (X(SEQ ID NO: 47) —NH₂) | 8–16 | 16–32 | 4 | 32–64 |
| 3 (X(SEQ ID NO: 48) —NH₂) | 4 | 8 | 4 | 32–64 |
| 5 (X(SEQ ID NO: 49) —NH₂) | 8 | 32 | 2 | 64–128 |
| 7 (X(SEQ ID NO: 50) —NH₂) | 4 | 4–8 | 2 | 64 |
| 9 (X(SEQ ID NO: 51) —NH₂) | 8 | 16 | 4 | 64 |
| 11 (X(SEQ ID NO: 52) —NH₂) | 64 | 8 | 2 | 256 |
| 12 (X(SEQ ID NO: 53) —NH₂) | 8 | 8 | 4 | 32 |
| 14 (X(SEQ ID NO: 54) —NH₂) | 8 | 8 | 2 | 32 |
| 16 (X(SEQ ID NO: 55) —NH₂) | 8 | 16 | 4 | 32 |
| 18 (X(SEQ ID NO: 56) —NH₂) | 16 | 8 | 2 | 32 |

EXAMPLE 12

Analogues of the parent peptide were prepared wherein at least amino acid residues 1–6 were deleted, or where at least four amino acid residues were linked to amino acid residue 1 of the complete parent peptide structure. These analogues are hereinafter referred to as analogues 1 through 7.

Analogue 1 has the following structure:
X(SEQ ID NO: 57).
Analogue 2 has the following structure:
X(SEQ ID NO: 58).
Analogue 3 has the following structure:
X(SEQ ID NO: 59).
Analogue 4 has the following structure:
X(SEX ID NO: 60).
Analogue 5 has the following structure:
X(SEQ ID NO: 61).
Analogue 6 has the following structure:
X(SEQ ID NO: 62).

-continued

Analogue 7 has the following structure:
X(SEQ ID NO: 63).

These analogues were then assayed for MIC with respect to *E. coli, P. aeruginosa, S. aureus* and *S. epidermidis*. The results are given in Table VIII below:

TABLE VIII

| Analogue | Minimum Inhibitory Concentration (μg/ml) | | | |
|---|---|---|---|---|
| | E. Coli | P. Aeruginosa | S. aureus | S. epidermidis |
| 1 | >256 | >256 | >256 | >256 |
| 2 | 128 | 64 | >256 | 64 |
| 3 | 32-64 | 32-64 | 256 | 2 |
| 4 | 128 | 128 | >256 | 32 |
| 5 | >256 | 256 | >256 | 64 |
| 6 | >256 | 256 | >256 | 128 |
| 7 | >256 | 256 | >256 | 128 |

EXAMPLE 13

The hemolytic activity of the parent peptide and the deletion analogues hereinabove described in Example 11 was examined with human red blood cells. Serum was separated from red blood cells through centrifugation, and the blood cells were washed with phosphate buffered saline (PBS) at a pH of 7. The PBS was removed by centrifugation. The cells were then suspended in PBS to reach a concentration of 5 percent cells in PBS. The peptides were dissolved in PBS and added to 0.5 ml of the red blood cell suspension to reach a final volume of 1 ml. Peptide concentrations are at 500 μg/ml, 100 μg/ml, 50 μg/ml, or 10 μg/ml. The samples of peptide and red blood cells are incubated for one hour at 37° C. The samples are then centrifuged for five minutes. The supernatant was separated from the pellet and the optical density of the supernatant was measured at 414 nm. No hemolysis (blank) and 100 percent hemolysis were determined from suspensions of cells in PBS and Triton 1 percent, respectively. Percent hemolysis was measured at peptide concentrations of 500 μg/ml, 100 μg/ml, 50 μg/ml μg/ml. The results are listed in Table IX below:

TABLE IX

| Amino Acid Residue Deleted | Percent Hemolysis Concentration of Peptide (μg/ml) | | | |
|---|---|---|---|---|
| | 500 | 100 | 50 | 10 |
| 1 (SEQ ID NO: 46) | 16.2 | 10.1 | 7.6 | 1.1 |
| 2 (SEQ ID NO: 47) | 22.4 | 15.0 | 11.0 | 1.3 |
| 3 (SEQ ID NO: 48) | 17.9 | 5.7 | 5.1 | 0.9 |
| 5 (SEQ ID NO: 49) | 60.7 | 49.7 | 34.4 | 12.1 |
| 7 (SEQ ID NO: 50) | 43.7 | 12.6 | 4.1 | 0.8 |
| 9 (SEQ ID NO: 51) | 75.3 | 49.9 | 33.0 | 11.7 |
| 11 (SEQ ID NO: 52) | 4.4 | 0.6 | 0.1 | 0.0 |
| 12 (SEQ ID NO: 53) | 50.3 | 31.5 | 18.0 | 2.6 |
| 14 (SEQ ID NO: 54) | 28.3 | 7.1 | 3.0 | 0.3 |
| 16 (SEQ ID NO: 55) | 24.9 | 25.4 | 20.1 | 2.5 |
| 18 (SEQ ID NO: 56) | 23.0 | 11.4 | 7.5 | 1.6 |
| None (SEQ ID NO: 3) (parent) | N/A | 21.3 | 16.1 | 3.4 |

EXAMPLE 14

Analogues 1 through 7, as hereinabove described in Example 12 were assayed for hemolytic activity in accordance with the procedures described in Example 13. The results are given below in Table X.

TABLE X

| Analogue | Percent Hemolysis Concentration of Peptide (μg/ml) | | | |
|---|---|---|---|---|
| | 500 | 100 | 50 | 10 |
| 1 (SEQ ID NO: 57) | 0.6 | 0.0 | 0.0 | 0.0 |
| 2 (SEQ ID NO: 58) | 0.4 | 0.0 | 0.0 | 0.0 |
| 3 (SEQ ID NO: 59) | 6.4 | 3.4 | 1.6 | 0.5 |
| 4 (SEQ ID NO: 60) | 45.7 | 27.2 | 18.8 | 4.3 |
| 5 (SEQ ID NO: 61) | 35.1 | 21.6 | 18.0 | 3.0 |
| 6 (SEQ ID NO: 62) | 26.6 | 24.9 | 18.2 | 2.0 |
| 7 (SEQ ID NO: 63) | 17.7 | 19.4 | 17.8 | 2.5 |

EXAMPLE 15—ANTIBACTERIAL ASSAY

The procedure for the following antibacterial assay is based upon the guidelines of the National Committee for Clinical Laboratory Standards, Document M7-T2, Volume 8, No. 8, 1988.

Stock solutions of the following Peptides (SEQ ID NO:4) and (SEQ ID NO:64) through (SEQ ID NO:68) in accordance with the present invention are prepared at a concentration of 512 μg/ml in sterile deionized distilled water and stored at −70° C.

(SEQ ID NO:64) is an analogue of the parent peptide wherein amino acid residues 1 through 5 have been deleted; (SEQ ID NO:65) is an analogue of the parent peptide wherein amino acid residues 1 through 4 have been deleted; (SEQ ID NO:66) is an analogue of the parent peptide wherein amino acid residues 1 through 3 have been deleted, (SEQ ID NO:67) is an analogue of the parent peptide wherein amino acid residues 1 through 7 have been deleted; and (SEQ ID No: 68) is an analogue of the parent peptide wherein amino acid residue 11 is substituted with a glycine residue. The peptides may be acetylated at the N-terminal as hereinabove described, such acetylation being indicated by the letter X.

The stock peptide solution was diluted in serial dilutions (1:2) down the wells of a microtiter plate so that the final concentrations of peptides in the wells were 0.25, 0.50, 1, 2, 4, 8, 16, 32, 64, 128, and 256 μg/ml. 1–5×10⁵ CFUs/ml of either *S. aureus* ATCC 25923, *E. coli* ATCC 25922, or *P. aeruginosa* ATCC 27853 were added to the wells in full strength Mueller Hinton broth (BBL 11443) from a mid-log culture. The inoculum is standarized spectrophotometrically at 600 nm and is verified by colony counts. The plates are incubated for 16–20 hours at 37° C., and the minimal inhibitory concentration (MIC) for each peptide is determined. Minimal inhibitory concentration is defined as the lowest concentration of peptide which produces a clear well in the microtiter plate. The results are given in Table XI below.

For purposes of explanation of Table XI below, S is the MIC of the peptide against *S. aureus*, P is the MIC of the peptide against *P. aeruginosa*, and E is the MIC of the peptide against *E. coli*.

TABLE XI

| Peptide | MIC (μg/ml) | | |
|---|---|---|---|
| | S | P | E |
| (SEQ ID NO: 4) —NH₂ | 32 | 64 | 32 |
| X-(SEQ ID NO: 4) —NH₂ | 32 | 64 | 32 |
| (SEQ ID NO: 64) —NH₂ | 32 | 16 | 32 |
| X-(SEQ ID NO: 65) —NH₂ | 16 | 16, 32 | 32 |
| X-(SEQ ID NO: 66) —NH₂ | 8 | 16 | 8 |
| (SEQ ID NO: 67) —NH₂ | 128 | 128 | 128 |
| X-(SEQ ID NO: 68) —NH₂ | 8 | 8 | 16 |

EXAMPLE 16

The procedure of Example 15 was repeated for assaying the antimicrobial activity of amide-terminated peptides (SEQ.ID NO:64) through (SEQ ID. NO:67). The results are given in Table XII below.

TABLE XII

| Peptide | MIC (μg/ml) | | |
|---|---|---|---|
| | S | P | E |
| (SEQ. ID. NO.: 64) —NH₂ | 8 | 8 | 16 |
| (SEQ. ID. NO.: 65) —NH₂ | 8 | 4 | 16 |

TABLE XII-continued

| Peptide | MIC (μg/ml) | | |
|---|---|---|---|
| | S | P | E |
| (SEQ. ID. NO.: 66) —NH₂ | 8 | 4 | 16 |
| (SEQ. ID. NO.: 67) —NH₂ | 8 | 32 | 16, 32 |

Numerous modifications and variations of the present invention are possible in light of the above teachings, and, therefore, within the scope of the accompanying claims, the invention may be practiced other than as particularly described.

We claim:

1. A process for inhibiting growth of a target cell comprising:
    administering to a host a biologically active amphiphilic peptide, said peptide including the following structural formula:

$R_1$-$R_1$-$R_2$-$R_1$-$R_1$-$R_2$-$R_2$-$R_1$-$R_1$-$R_2$-$R_2$-$R_1$-$R_2$-$R_2$, wherein -$R_1$ is a hydrophobic amino acid, and -$R_2$ is a basic hydrophilic or neutral hydrophilic amino acid, said peptide being administered in an amount effective to inhibit growth of a target cell in a host, wherein said hydrophobic amino acids are selected from the group consisting of Ala, Cys, Phe, Gly, Ile, Leu, Met, methionine sulfoxide, Val, Trp, and Tyr; said basic hydrophilic amino acids are selected from the group consisting of Lys, Arg, His, orn, homoarginine 2,4-diaminobutyric acid, and p-aminophenylalanine; and said neutral hydrophilic amino acids are selected from the group consisting of Asn, Gln, Ser, and Thr.

2. The process of claim 1 wherein said peptide has the following structural formula:

(SEQ ID NO:1).

3. A process for inhibiting growth of a target cell comprising:
    administering to a host a biologically active amphiphilic peptide, said peptide including the following structural formula:

$R_2$-$R_1$-$R_1$-$R_2$-$R_2$-$R_1$-$R_2$-$R_2$-$R_1$-$R_1$-$R_2$-$R_2$-$R_1$-$R_1$, wherein $R_1$ is a hydrophobic amino acid, and $R_2$ is a basic hydrophilic or neutral hydrophilic amino acid, said peptide being administered in an amount effective to inhibit growth of a target cell in a host, wherein said hydrophobic amino acids are selected from the group consisting of Ala, Cys, Phe, Gly, Ile, Leu, Met, methionine sulfoxide, Val, Trp, and Tyr; said basic hydrophilic amino acids are selected from the group consisting of Lys, Arg, His, orn, homoarginine 2,4-diaminobutyric acid, and p-aminophenylalanine; and said neutral hydrophilic amino acids are selected from the group consisting of Asn, Gln, Ser, and Thr.

4. The process of claim 3 wherein said peptide has the following structural formula:

(SEQ ID NO:2).

5. A biologically active amphiphilic peptide, said peptide being of the following structural formula:

$R_1$-$R_2$-$R_1$-$R_1$-$R_2$-$R_2$-$R_1$-$R_1$-$R_2$-$R_2$-$R_1$-$R_2$-$R_2$-$R_1$, wherein $R_1$ is a hydrophobic amino acid, and $R_2$ is a basic hydrophilic or neutral hydrophilic amino acid, wherein said hydrophobic amino acids are selected from the group consisting of Ala, Cys, Phe, Gly, Ile, Leu, Met, methionine sulfoxide, Val, Trp, and Tyr; said basic hydrophilic amino acids are selected from the group consisting of Lys, Arg, His, orn, homoarginine 2,4-diaminobutyric acid, and p-aminophenylalanine; and said neutral hydrophilic amino acids are selected from the group consisting of Asn, Gln, Ser, and Thr.

6. The peptide of claim 5 wherein said peptide has the following structural formula:

(SEQ ID NO:3).

7. A process for inhibiting growth of a target cell, comprising:
    administering to a host a biologically active amphiphilic peptide, said peptide being of the following structural formula:

$R_1$-$R_2$-$R_1$-$R_1$-$R_2$-$R_2$-$R_1$-$R_1$-$R_2$-$R_2$-$R_1$-$R_2$-$R_2$-$R_1$-$R_1$-$R_2$-$R_2$-$R_1$, wherein $R_1$ is a hydrophobic amino acid, and $R_2$ is a basic hydrophilic or neutral hydrophilic amino acid, said peptide being administered in an amount effective to inhibit growth of a target cell in a host, wherein said hydrophobic amino acids are selected from the group consisting of Ala, Cys, Phe, Gly, Ile, Leu, Met, methionine sulfoxide, Val, Trp, and Tyr; said basic hydrophilic amino acids are selected from the group consisting of Lys, Arg, His, orn, homoarginine, 2,4-diaminobutyric acid, and p-aminophenylalanine; and said neutral hydrophilic amino acids are selected from the group consisting of Asn, Gln, Ser, and Thr.

8. The process of claim 7 wherein said peptide has the following structural formula:

(SEQ ID NO:3).

9. A compound, comprising:
    an analogue of a peptide, said peptide being in an amide- or carboxy-terminated form, said peptide being represented by the following structural formula, and the numbers below each amino acid residue refer to the position of the residue in the peptide: LeuLysLeuLeuLysLysLeuLeuLysLys-LeuLysLysLeuLeuLysLysLeu 1 2 3 4 5 6 7 8 9 10 11 12 13 14 15 16 17 18 and wherein said peptide is substituted in at least one of positions 1, 3, 4 and 7–18 as follows:

| Residue No. | Substituent |
|---|---|
| 1 | Methionine sulfoxide, Lys, or Met |
| 3 | Methionine sulfoxide, Lys, or Met |
| 4 | Methionine sulfoxide, Lys, Met, His, Ser, or Arg |
| 7 | Methionine sulfoxide, Lys, or Met |
| 8 | Methionine sulfoxide, Lys, or Met |
| 9 | Methionine sulfoxide |
| 10 | Methionine sulfoxide |
| 11 | Methionine sulfoxide, Met, Ser, Lys, Arg, His, or Gly |
| 12 | Methionine sulfoxide |
| 13 | Methionine sulfoxide, or Met |
| 14 | Methionine sulfoxide, Lys, or Met |
| 15 | Methionine sulfoxide, Lys, or Met |
| 16 | Methionine sulfoxide |
| 17 | Methionine sulfoxide |
| 18 | Methionine sulfoxide, or Met |

10. The compound of claim 9 wherein at least one of amino acid residues 1, 7, 8, 11, 14, 15, and 18 is substituted with methionine sulfoxide.

11. The compound of claim 9 wherein at least one of amino acid residues 1, 7, 8, 14, 15, and 18 is substituted with methionine sulfoxide.

12. The compound of claim 9 wherein at least one of amino acid residues 4, 7, 8, 11, and 14 is substituted with a lysine residue.

13. The compound of claim 9 wherein amino acid residues 4 is substituted with a methionine residue.

14. The compound of claim 9 wherein at least one of amino acid residues 4 and 11 is substituted with an arginine residue.

15. The compound of claim 9 wherein at least one of amino acid residues 4 and 11 is substituted with a histidine residue.

16. A process of inhibiting the growth of a microbe in a host, comprising:
administering to a host an effective anti-microbial amount of the compound of claim 9.

17. A process of inhibiting the growth of a tumor in a host, comprising:
administering to a host an effective anti-tumor amount of the compound of claim 9.

18. A compound comprising:
an analogue of a peptide, said peptide being in an amide- or carboxy-terminated form, said peptide being represented by the following structural formula, and the numbers below each amino acid residue refer to the position of the residue in the peptide: LeuLysLeuLeuLysLysLeuLeuLysLys-LeuLysLysLeuLeuLysLysLeu 1 2 3 4 5 6 7 8 9 10 11 12 13 14 15 16 17 18 and wherein at least one of amino acid residues 1 through 7, 9, 11, 12, 14, 16, or 18 is deleted from said peptide.

19. The compound of claim 18 wherein at least one of amino acid residues 3, 7, 11, 14 or 18 is deleted from said peptide.

20. The compound of claim 18 wherein amino acid residues 1 through 3 are deleted from said peptide.

21. The compound of claim 18 wherein amino acid residues 1 through 4 are deleted from said peptide.

22. The compound of claim 18 wherein amino acid residues 1 through 6 are deleted from said peptide.

23. The compound of claim 18 wherein amino acid residues 1 through 7 are deleted from said peptide.

24. A process of inhibiting the growth of a microbe in a host, comprising: administering to a host an effective anti-microbial amount of the compound of claim 18.

25. A process of inhibiting the growth of a virus in a host, comprising: administering to a host an effective anti-viral amount of the compound of claim 18.

26. A process of inhibiting the growth of a tumor in a host, comprising: administering to a host an effective anti-tumor amount of the compound of claim 18.

27. A biologically active amphiphilic peptide, said biologically active amphiphilic peptide including the following structural formula $Y_{10}$:

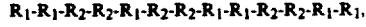

$R_1\text{-}R_1\text{-}R_2\text{-}R_2\text{-}R_1\text{-}R_2\text{-}R_2\text{-}R_1\text{-}R_1\text{-}R_2\text{-}R_2\text{-}R_1\text{-}R_1$, wherein $R_1$ is a hydrophobic amino acid, and $R_2$ is a basic hydrophilic or neutral hydrophilic amino acid, wherein said hydrophobic amino acids are selected from the group consisting of Ala, Cys, Phe, Gly, Ile, Leu, Met, methionine sulfoxide, Val, Trp, and Tyr; said basic hydrophilic amino acids are selected from the group consisting of Lys, Arg, His, orn, homoarginine, 2,4-diaminobutyric acid, and p-aminophenylalanine; and said neutral hydrophilic amino acids are selected from the group consisting of Asn, Gln, Ser, and Thr.

28. The peptide of claim 27 wherein said peptide includes the following structure:
$Y_{10}\text{-}Z_{10}$, wherein $Y_{10}$ is the peptide structure of claim 27, and $Z_{10}$ is:
(i) $R_2$;
(ii) $R_2\text{-}R_1$; or
(iii) $R_2\text{-}R_1\text{-}R_1$.

29. The peptide of claim 28 wherein said peptide includes the following structural formula:

(SEQ ID NO:4).

30. A process of inhibiting the growth of a microbe in a host, comprising:
administering to a host an effective anti-microbial amount of the peptide of claim 27.

31. A process of inhibiting the growth of a tumor in a host, comprising:
administering to a host an effective anti-tumor amount of the peptide of claim 27.

* * * * *